United States Patent [19]

Gatewood

[11] Patent Number: 4,813,869

[45] Date of Patent: Mar. 21, 1989

[54] JAW FIXATION ASSEMBLY

[76] Inventor: John B. Gatewood, 5200 Meadowcreek Dr., Apt. 1118, Dallas, Tex. 75248

[21] Appl. No.: 21,459

[22] Filed: Mar. 4, 1987

Related U.S. Application Data

[63] Continuation-in-part of Ser. No. 864,006, May 16, 1986, abandoned.

[51] Int. Cl.[4] ............................................. A61C 3/00
[52] U.S. Cl. ...................................... 433/18; 128/89 A
[58] Field of Search ................... 433/18, 19, 178, 39, 433/149, 225; 128/89 A

[56] References Cited

U.S. PATENT DOCUMENTS

| | | | |
|---|---|---|---|
| 1,638,006 | 9/1927 | Aderer | 128/89 |
| 2,481,177 | 9/1949 | Tofflemire | 128/89 |
| 2,502,902 | 4/1950 | Tofflemire | 128/92 |
| 3,434,209 | 3/1969 | Weissman | 433/225 |
| 3,482,314 | 12/1969 | Tofflemire | 433/18 |
| 3,803,715 | 4/1974 | Wallshein | 433/20 |
| 3,829,975 | 8/1974 | Balson | 433/39 |
| 3,913,228 | 10/1975 | Wallshein | 433/18 |
| 3,964,165 | 6/1976 | Stahl | 433/14 |
| 4,090,299 | 5/1978 | Williams | 433/18 |
| 4,202,328 | 5/1980 | Sukkarie | 128/89 |
| 4,230,104 | 10/1980 | Richter | 128/89 |
| 4,242,085 | 12/1980 | Wallshein | 433/14 |
| 4,318,694 | 3/1982 | Klein | 433/18 |
| 4,384,854 | 5/1983 | Garfinkel | 433/215 |

FOREIGN PATENT DOCUMENTS

| | | | |
|---|---|---|---|
| 601835 | 8/1934 | Fed. Rep. of Germany | 433/18 |
| 2855996 | 8/1979 | Fed. Rep. of Germany | 433/18 |

*Primary Examiner*—John J. Wilson
*Attorney, Agent, or Firm*—Hubbard, Thurman, Turner & Tucker

[57] ABSTRACT

The invention has an anchor member mounted around and on one or more teeth on each jaw, which are adjustably and removably mounted thereon by retainer members. The retainer members have a body member with an axial bore and an additional bore transverse to the axial bore or a peripheral groove for ligature wires in order to fix the device mounted on the lower jaw to a similar device mounted on the upper jaw in roughly vertical alignment therewith. Crosswiring the retainer members between jaws provides a solid unmovable jaw fixation assembly. An alternative embodiment provides a strap member which allows the anchor members to be mounted on isolated or semi-isolated teeth.

30 Claims, 3 Drawing Sheets

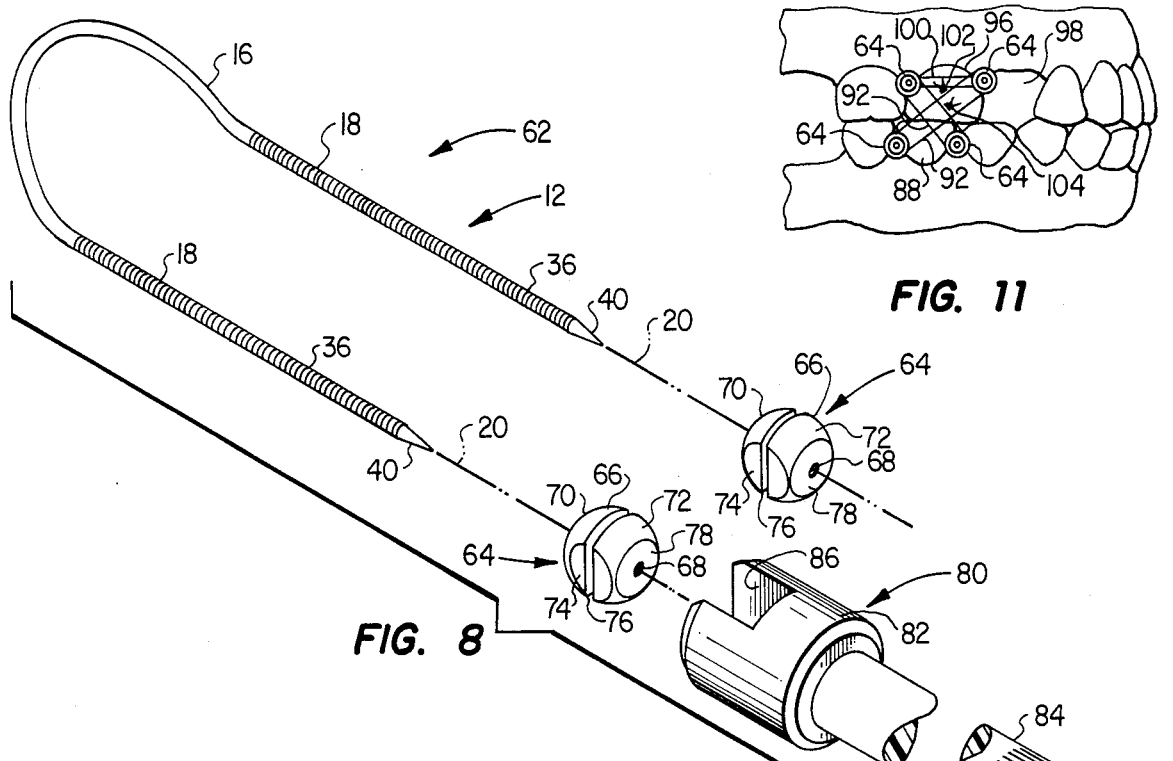
FIG. 11
FIG. 8
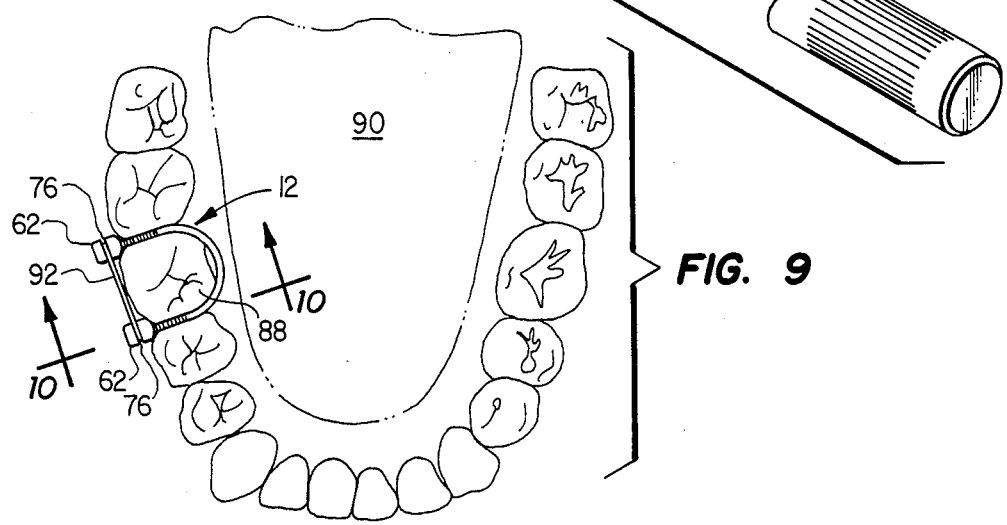
FIG. 9
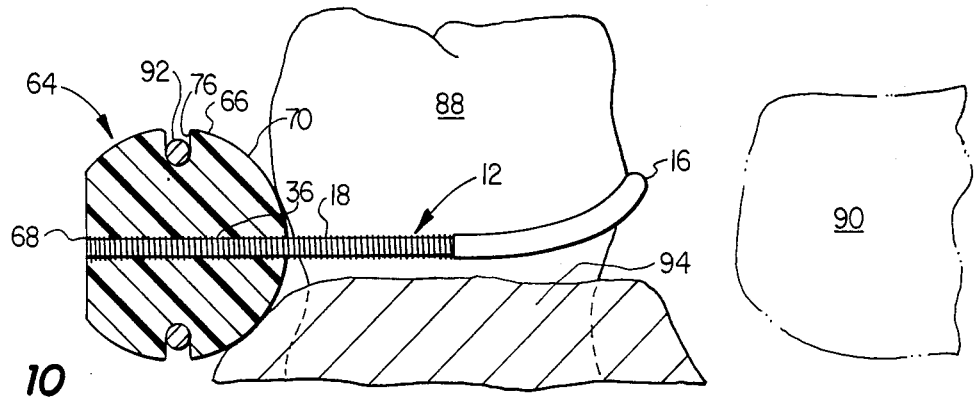
FIG. 10

JAW FIXATION ASSEMBLY

This application is a Continuation-In-Part of U.S. application Ser. No. 864,006 by the same inventor filed May 16, 1986 and now abandoned, for which benefit is claimed under 35 U.S.C. §120.

BACKGROUND OF THE INVENTION

1. Field of the Invention

The invention pertains to a jaw fixation assembly for use in the oral and maxillofacial surgery art to immobilize the jaw structure after corrective surgery or trauma. The assembly includes anchor members mounted around a tooth on each jaw by easily adjustable and removable retainer members. The retainer members provide a place for cross-wiring the jaws together.

2. Background

In the art of oral and maxillofacial surgery there have been several developments toward the provision of structures for stabilizing the upper and lower jaws after corrective surgery or trauma. A conventional way of immobilizing either the maxillary or mandibular structures is to provide elongated bars, such as arch bars, which are secured to the buccal and labial faces of certain ones of the teeth. The securing of arch bars with fine wires wrapped around certain ones of the teeth is particularly disadvantageous in that affixation of the wires takes considerable time to perform, during which the patient is often under a general anesthetic and is exposed to the hazards associated therewith. Moreover, the wires frequently break, are uncomfortable and are prone to trapping food particles. Other techniques include the provision of several small brackets which are secured to select ones of the teeth and then interconnected by a complex set of arch wires. In certain instances, the arch wires are strung between the upper and lower tooth sets to fix the jaw in a permanently closed condition until the corrective or healing process is complete.

The procedure in attaching the aforementioned brackets, and stringing the arch wires is complicated and often results in structural failure of the parts thereby requiring second and third efforts to rebuild the structure before the corrective process is complete. Moreover, the complex structures associated with the prior art apparatus are often bulky uncomfortable and irritating to the gingiva and other mouth tissues and tend to trap food particles resulting in the adverse affects caused thereby. They may also cause damage to tooth enamel. Wedge-like devices can tend to separate adjacent teeth. Pain and discomfort to the patient caused by present prior art devices are a major problem that needs to be overcome.

Accordingly, there has been a continuing need to improve jaw fixation devices to achieve ease of constructing a system to immobilize the jaw structure. There has also been a need for a jaw fixation system wherein the structure is mechanically simple and not subject to failure but which is easily adjusted for use with each patient and does not require a substantial amount of time to install the structure in the patient's mouth. Moreover, the simpler the fixation structure the less likelihood of mechanical failure or the provision of surfaces which will cause pain, irritation, discomfort or accumulate food particles or the like. The present invention provides these and other advantages. In the event of post-operative complications which may arise, the prior art devices take a long time to remove and replace because of the multitude of wires that must be cut and replaced to disengage and reengage the jaw immobilization devices. The device of the invention accomplishes jaw fixation more quickly and easily than prior devices with fewer parts.

SUMMARY OF THE INVENTION

The present invention provides an improved jaw fixation assembly for temporary fixation of the upper and lower jaw structure after corrective surgery or trauma.

In accordance with one aspect of the invention a generally "U" shaped anchor member is attached to at least one tooth on the lower jaw and a similar anchor member is attached to at least one tooth on the upper jaw in generally vertical alignment so that the jaws can be wired, preferably cross-wired, together to immobilize the jaws. The anchor member is essentially a strong wire member with a collar portion which is placed around the inside or lingual surface of the tooth preferably in contact with the cervical neck between the crown and the root of the tooth, above the gum line. The curved portion joins a pair of straight leg portions of the wire which are spaced apart by the width of an average tooth. The straight portions are passed through the interproximal spaces between one selected tooth and its adjacent teeth and the ends of the anchor member wire extend outwardly of the tooth-jaw line extending towards the cheek. The straight portions of the anchor members have a means for attaching on each one a retainer member, which has an outside end away from the inside of the mouth and which has a rounded inside end which is fixed on the anchor member up against the tooth and gingiva and can be tightened and loosened or even removed. The excess portion of the straight portion of the anchor member is cut flush with the outer end of the retainer member when the device is installed so as to avoid any sharp edges. The body of the retainer member has additional cross bores which serve as sites for ligature wire which joins the upper and lower fixation devices to immobilize the jaws. The ligature wires thus also serve to prevent the retainer members from rotating or otherwise coming loose.

Another aspect of the invention has a modified means for retaining the anchor member securely to selected teeth. The retainer members have a body portion with an axial bore extending therethrough to engage the straight portion of the anchor member. Aligned generally with the openings at the inner and outer portions of the bore are rounded inner and outer ends of the body, one which can be tightened up against the teeth. A peripheral groove extends around the body portion between the ends of the body, which serves as a convenient place to fix the location of ligature wires that are used between opposed retainer members in the upper and lower jaw to fix the jaws in the closed position. A flattened area or areas on the body portion of the retainer members may be used as a place for engagement of a tool which is used to turn individual retainer members.

Another embodiment has the same structure as indicated in the preceeding paragraph except that a separate flexible ring, such as an "O" ring is installed over the leg ends of the anchor members and between the tooth and the retainer members, one for each juncture. When the retainer members are screwed or otherwise tightened against the tooth, the O ring is compressed and it provides cushioning and shock resisting properties as well as insulating properties both electrical and thermal to minimize the effect of heat or cold and also to minimize generation of galvanic currents by contact of dissimilar metals in the electrolyte environment of the mouth.

In yet another modification the same basic device is used comprising the anchor members and retainer members but in place of the O rings a strap is installed with an opening for each of the straight leg portions of each anchor member in order to provide appropriate anchoring where there is a gap between the tooth upon which anchoring is to be based and adjacent teeth. The anchor member is placed around the selected tooth with the straight portions pointed outward and the curved portion against the lingual side of the tooth. The openings in the strap are each pushed over one of the legs of an anchor member and the strap is placed up against the buccal side of the selected tooth and the retainer members are fastened to the straight portions of the anchor members up against the strap member. Upon tightening the retainer members on the selected tooth the strap is tensioned along with the anchor member itself. Devices so mounted upon a selected tooth of each jaw may be joined together to fix the jaws in the usual manner. The strap also is preferably deformable and nonmetallic to follow the contours of the tooth and to aid in thermal and electrical insulation as indicated above. Alternately, wire may be passed around opposed straight legs of a given anchor member between the tooth and the retainer members to keep the anchor member from opening up as the retainer members are tightened on a tooth without an adjacent tooth.

Those skilled in the art will recognize that the fixation assembly of the present invention is structurally uncomplicated, utilizes components which may be manufactured of low cost relatively inert materials suitable for placement in the oral cavity and which are less susceptible to structural failure or trapping food particles and other substances present in the mouth than has been provided by prior art jaw fixation structures. The device of the invention is easier and quicker to install or to remove and reinstall in the event of post-operative complications. Those skilled in the art will further appreciate the above described features and advantages of the present invention as well as additional superior aspects thereof upon reading the detailed description which follows in conjunction with the drawing.

BRIEF DESCRIPTION OF THE DRAWINGS

FIG. 8 is an exploded perspective view of the anchor member with modified retainer members and a tool to engage the retainer members for tightening;

FIG. 9 is a plan view of a jaw showing one of the devices with the modified retainer members;

FIG. 10 is a partially sectioned front elevation view through the line 10—10 from FIG. 9;

FIG. 11 is a side elevation with two of the devices of FIGS. 8, 9 and 10 mounted and cross-wired between jaws. Wires are used to aid in fixing the invention to the tooth of the upper jaw having a missing adjacent tooth.

DESCRIPTION OF THE PREFERRED EMBODIMENTS

Figure 1:
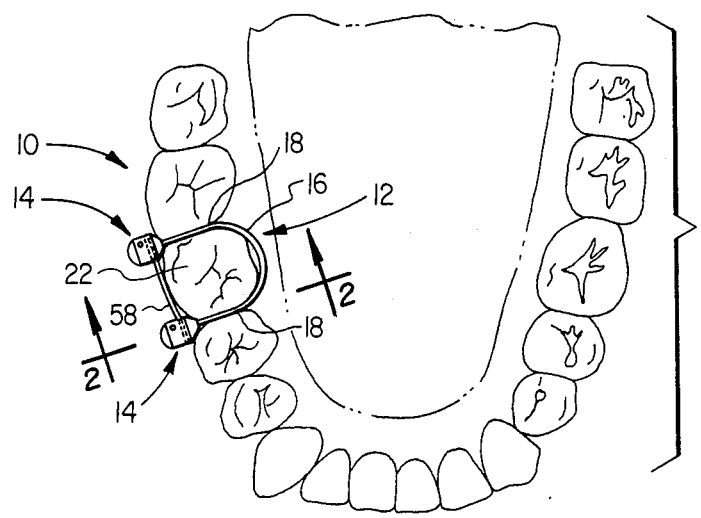
FIG. 1 is a plan view of a fixation device mounted on a tooth of one jaw.

In the description which follows like parts are marked throughout the specification and drawings with the same reference numerals, respectively. The drawing figures are not necessarily to scale and certain elements of the fixation system may be shown exaggerated in scale in the interest of clarity.

Figure 2:
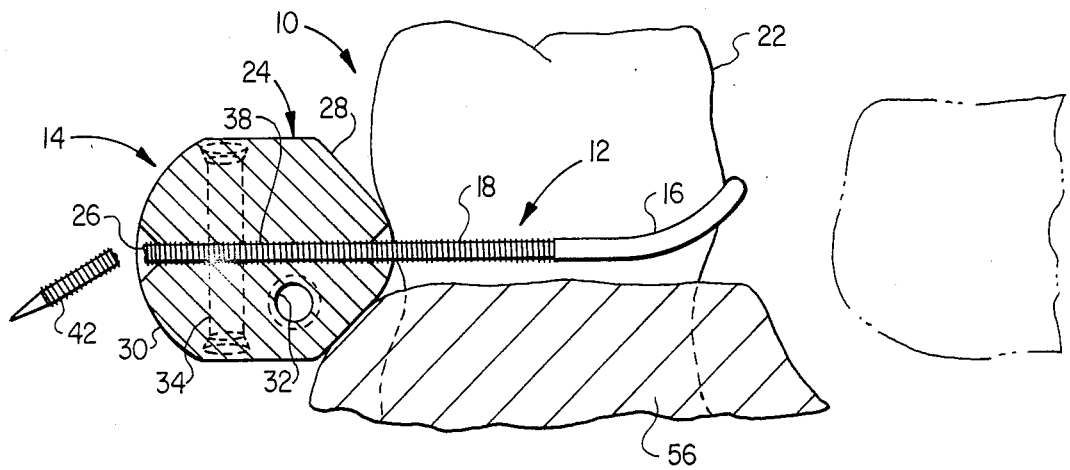
FIG. 2 is a detailed view, partially sectioned, in an elevation of a portion of the device shown in FIG. 1.
Figure 4:
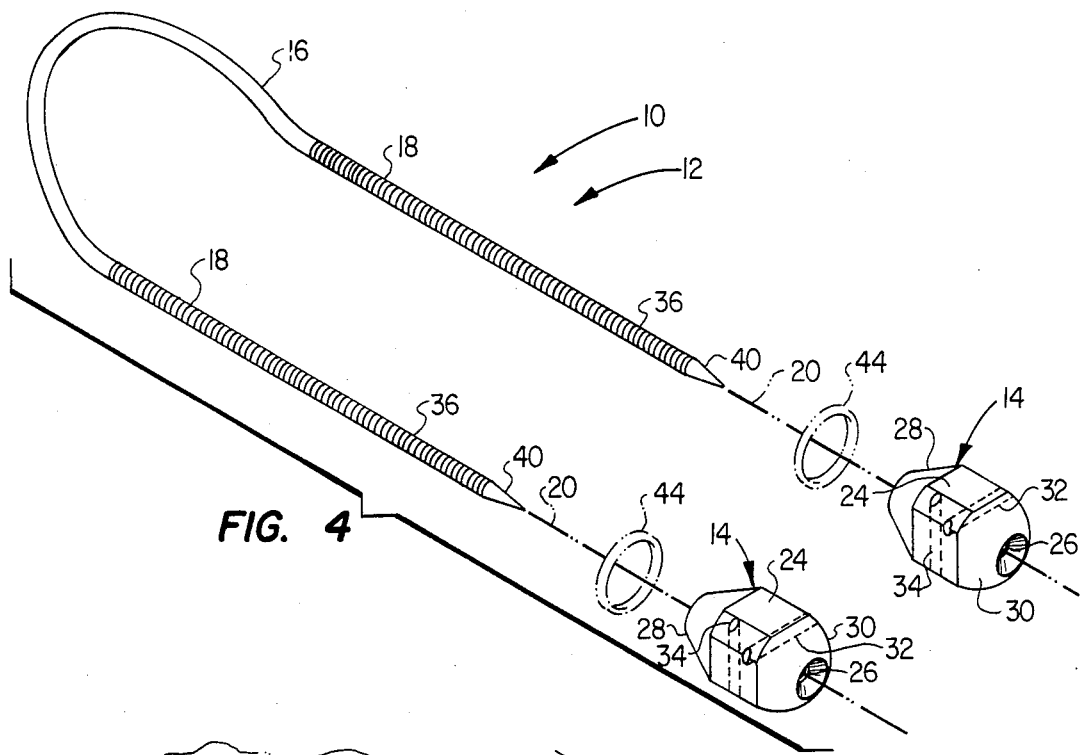
FIG. 4 is an exploded perspective view of one of the devices of the invention.

Referring to FIGS. 1, 2 and 4, the dental fixation device of the present invention is generally designated by the numeral 10 and comprises an anchor member 12 and a retainer member 14.

In FIG. 4 the anchor member 12 has a collar portion 16 and straight leg portions 18. The straight portions 18 of the anchor member are joined by the collar portion 16 in a generally "U" shaped configuration. Each of the straight leg portions 18 has an axis 20 which together define a plane which may be thought of as generally horizontal because of the orientation of the system 10 when it is used in the jaw of a patient. The collar portion 16 in addition to being curved so as to be able to go around a tooth as indicated in FIG. 1, is also curved away from the plane defined by the axes 20 of the straight leg portions of the anchor member. This may be referred to as an upward curvature away from the axes of the straight leg portions and its purpose will be discussed later.

With the anchor member 12 placed about a tooth 22 in FIG. 1 with the collar portion against the lingual side of the selected tooth, the straight portions 18 extend outwardly from the lingual aspect of the tooth and lie adjacent to the sides of said tooth around which the collar 16 partially extends. The portions 18 extending interproximally through the spaces between the teeth have an outwardly extending excess portion. The excess portion will vary depending upon the size of the tooth since the collar should be resting against the lingual tooth surface and the straight portions will pass through the interproximal spaces and beyond the buccal side of the selected tooth. Enough excess should be provided to accommodate even the largest expected tooth with knowledge that the excess will be removed to complete the installation.

Retainer members 14 have a body portion 24 having an axial bore 26 extending completely therethrough and which as will be seen will be axially aligned with the axis 20 of the straight portion 18 in use. It has a rounded inner portion 28 and an outer portion 30 which may also preferably be rounded. Retainer member 14 also has one or more transverse ligature bores 32 and 34 which are best seen in FIG. 2. Transverse bores 32 and 34 extend all the way through the body and are offset from the axis of bore 26. Bores 32 and 34 are preferably at right angles to each other and of course they have an axis at approximately right angles to the axis 20 and bore 26.

Each straight portion 18 of anchor member 12 has a means 36 for removably engaging and disengaging with retainer member 14 which has a corresponding engaging means 38 extending through the bore 26 which allows a member 14 to be fixed on each straight leg portion 18 of anchor member 12. The straight portions 18 preferably have points 40 at their ends to aid in passing portions 18 through the interproximal spaces of the teeth and to aid in placing the retainer members 14 onto the straight portion 18 of anchor member 12. The bore at rounded portion 28 of members 14 may be chamfered to further aid in assembly. In assembly as shown in FIG. 2 the straight portions 18 have an excess portion 42 which is removed after installing retainer member 14 so as to avoid any sharp edges in the patients mouth area.

"O" rings 44 may be placed on each straight leg portion 18 before the members 14 are installed in order to provide a shock absorbing and insulating effect when the parts are assembled against a tooth, said rings being smaller than the body of the member 14 and provide a cushion between the retainer member 14 and the tooth and gingiva when the retainer members are tightened against a tooth. The "O" rings are preferably made of solid construction as opposed to hollow construction in a semi-hard rubber or elastomeric material that will partly compress when stressed by the tightening of the retainer members against them but will have sufficient compressive strength to allow a tight "lock" on the teeth when the anchor member and retainers are tightened. The "O" rings should not split or stretch out of the way. A tight lock should be obtained with some compressions in the "O" ring itself.

Figure 6:
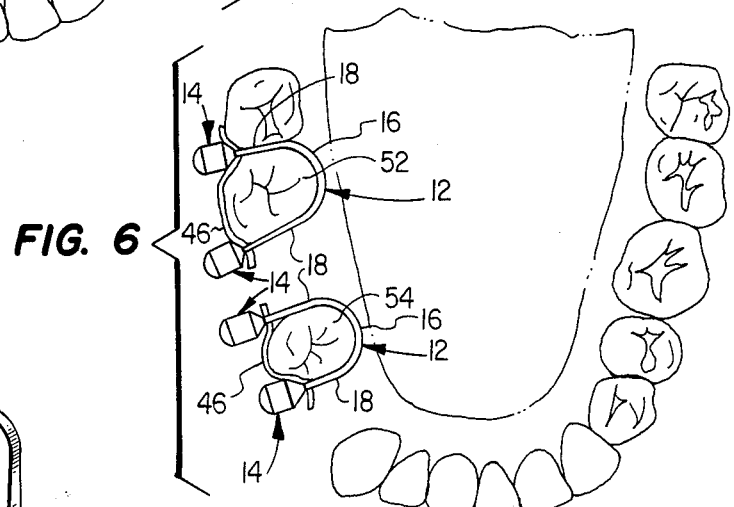
FIG. 6 is a plan view of a jaw which has missing teeth which illustrates the use of a modified form of the invention.
Figure 7:
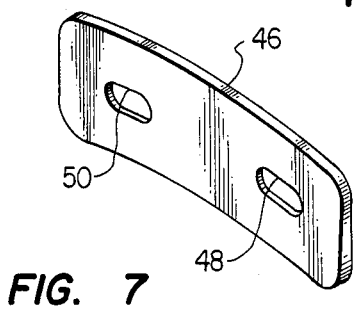
FIG. 7 is a perspective view of a deformable strap used with the device of FIG. 4 in FIG. 6.

In an alternative embodiment illustrated in FIGS. 6 and 7, bands 46 are provided which are deformable to follow the contour of a tooth. Band 46 has spaced apart openings 48 and 50 which are elongated in the length direction of the band to allow for some variation in the width of the teeth. As seen in FIG. 6 tooth 52 is illustrated as having one adjacent tooth but also having a gap opposite said adjacent tooth, as for example where a tooth had previously been removed. Anchor member 16 is placed with its collar portion against the lingual side of tooth 52 in the manner illustrated in FIG. 2. The band 46 is placed on the outside or buccal side of the tooth with straight portions 18 extending through the openings, 48 and 50 respectively and with retainer members 14 installed on straight portions 18 up against the band 46 which in turn rests against the outside or buccal surface of the tooth 52. Tightening of the retainer members 14 tensions the band as well as the anchor member 12 to securely mount the device of the invention in place on tooth 52 in spite of the fact that there is a gap or opening in the tooth line in the jaw as illustrated. A similar situation exists with respect to tooth 54 which is illustrated as having a gap on either side of it. The anchor member 12 is again placed around the tooth in the manner as previously described and illustrated generally in FIG. 2 with the band 46 on the outside of the tooth having straight portions 18 extending through the openings 48 and 50. Retainer members 14 are again fastened up against the band 46 on the portions 18 of the anchor member 12 and when tightened they tension the band 46 as well as the anchor member 12. The deformable member 46 follows the irregular contour of the tooth 54 as indicated in FIG. 6 to securely fasten the device to the tooth 54.

FIG. 8 illustrates the dental fixation assembly 62 which uses the same anchor member 12 as was previously described as part of fixation assembly 10. Like assembly 10 of FIG. 4 and subsequent figures, assembly 62 includes means for retaining anchor member 12 tightly against and around a selected tooth. The means for holding or retaining used in assembly 62 is a modified version of retainer member 14 which is called generally retainer member 64. Retainer member 64 has a body portion 66 having an axial bore 68 extending therethrough which in use will be axially aligned with axis 20 of straight leg portion 18 of anchor member 12. One such retainer is used for each leg of the anchor member.

Retainer member 64 has a rounded inside portion 70 and a rounded outside portion 72 of body portion 66. Body portion 66 has opposed flat surfaces 74 on either side of the bore 68 and generally parallel to its axes. One of the flat surfaces 74 on each body 66 is hidden in FIG. 8 while the opposite one is seen. A peripheral groove 76 is located in the body portion 66 between the rounded end portions 70, 72. The plane of a section through groove 76 would be approximately perpendicular to the axis of the bore 68. Groove 76 preferably goes all around the body of retainer member 64 including the opposed flat surfaces 74. Body member 66 may have a truncated portion 78 on the outside of body 66. The term inside our outside is meant in relation to the proximity to the tooth on which the retainer member is mounted, the inside being the part in contact with a selected tooth.

A tool generally designated 80 has a head portion 82 and a handle portion 84 preferably of generally cylindrical shape. Head portion 82 has a slot 86 which fits snugly over and against opposed flat surfaces 74 of the retainer members to provide a means for rotating the retainers 64.

FIG. 9 is a plan view of a lower jaw showing how the assembly of FIG. 8 looks when applied to a selected tooth 88 lying along with other teeth outside tongue 90. Anchor member 12 surrounds the tooth 88 with its straight leg portions passing between the interproximal spaces of tooth 88 and the teeth adjacent to it, as before. Retainer members 64 are tightened on anchor member 12 up against the outside of tooth 88 and its adjacent teeth low in the interproximal openings. It is similarly located when fastened to a selected opposed tooth on the upper jaw. The ligature wire 92 is shown for illustrative purposes only as being located in grooves 76 but because of the view it is not truly represented. The ligature wires 92 as they actually appear are shown in FIG. 11. They are simply wound around a retainer member of each respective upper and lower jaw anchor member as shown in FIG. 11 and the wire twisted to tighten. The grooves 76 (or transverse bores) keep the ligature wire conveniently in place.

FIG. 10 is a front elevation showing tooth 88 and gingiva 94 surrounding its base. Anchor member 12 has its curved portion 16 tight against the lingual side of tooth 88 with its upwardly curving portion away from the gingiva on the inside of the tooth line adjacent the tongue 90. Retainer member 64 has been rotated onto the means for engaging 36 on straight leg portion 18 and has its rounded portion 70 tightened against the buccal side of tooth 88 and its adjacent tooth (not shown) and is shown in limited partial contact with the gingiva on the outside of the tooth line. Even if the retainer member 64 is rotated upwardly by means of stress in ligature wire 92 applied through contact with groove 76, the upward curvature of collar portion 16 still prevents anchor member 12 from causing discomfort or soft tissue damage from contact with gingiva on the inside of the mouth.

FIG. 11 shows the device of FIGS. 8, 9 and 10 in completed assembly to wire the jaws shut. Each of selected lower tooth 88 and selected nearly opposed upper tooth 96 have in place an anchor member 12 behind them as in FIG. 10 except that collar portion 16 is reversed on tooth 96 in that the portion bent away from the plane of the axis 20 of the straight leg portions 18 is bent downward away from the roof of the mouth and the gingiva on the lingual side. The retainer members 64 are tightened. The upper jaw has a missing tooth 98 which provides no support so the straight leg portions 18 of the upper anchor member are wired across the outside surface of the tooth by wire 100 which lies under the uppermost retainer members adjacent the tooth. Wire 100 is fixed by knot 102. This prevents the legs 18 of the anchor member which pass around tooth 96 from spreading open as the retainer members are tightened. Means for binding a retainer member on one jaw to a retainer member on the opposite jaw are provided by ligature wires 92 cross-wired in the form of an "X" by placing them in the respective grooves 76 as shown and fixing them with a knot, such as knot 104. This arrangement provides resistance against both vertical and horizontal movement so that the jaws can remain fixed during the healing process. All knots are bent in so as to avoid contact with the lips or cheeks and for the same reason the tips 40 are severed as in FIG. 10 once the installation is completed. The method of using horizontal wires 100 when there is a vacant tooth on one or both sides of a selected tooth is preferred over the alternative shown in FIGS. 6 and 7.

Retainer members 14 or 64 are preferably made from a relatively hard plastic such as that sold in the trade under the name of "Delrin". The axial bore of the retainer members can be threaded but need not be since the bores 26 and 68 may be sized slightly less than the diameter of the legs 18 so that the retainer members may adapt to the threads thereon and provide sufficient holding when they are threaded onto legs 18. Threads are preferred though it should be recognized that alternate fastening means could be used also.

Referring now to FIGS. 1 through 6, in operation anchor member 12 is installed at a selected tooth by running the pointed end portions of straight leg portions 18 on either side of a tooth such as tooth 22 illustrated in FIG. 2. The collar portion 16 is placed with its upwardly curving portion away from the gingiva 56 in FIG. 2 and may be slightly bent as necessary to conform to the shape of the tooth so that collar portion 16 will tend to contact as much of the tooth portion as possible. Naturally because teeth have different widths it may be necessary to bend the collar portion slightly so that the straight portions 18 and the spaced apart axis 20 are closer together or further apart. A retainer member 14 is installed on each straight portion 18 of anchor member 12 and tightened snugly with the rounded inner portion 28, respectively, up against a tooth such as tooth 22 and/or part of the gingiva 56. Once both of the retainer members 14 are in place the excess portions 42 are cut off leaving a smooth surface. The outer portion 30 is preferably rounded and sharp edges must be avoided. Threads on the straight portions 18 of the anchor members are the preferred means of fastening the retainer members along with corresponding threads in each retainer member which preferably extend through the entire bore 26 in order to maximize holding power and avoid unnecessary cavities.

Figure 3:
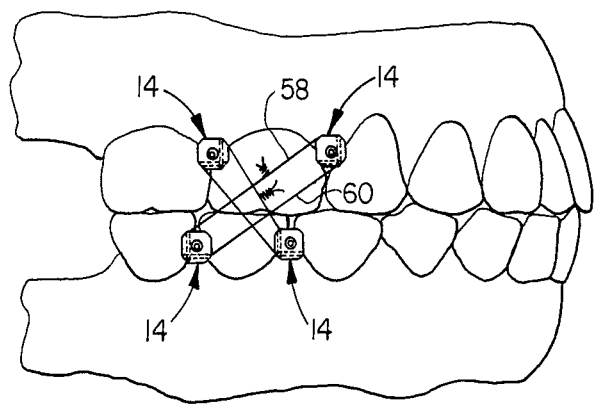
FIG. 3 is a side elevation with one of the devices in place on a tooth of each jaw which shows how the jaws are wired together.

A corresponding installation is made on a tooth in the opposite jaw in a generally vertical orientation as illustrated in FIG. 3. Even after the excess material 42 is removed the retainer members can be tightened or loosened as necessary to alter the fit. The collar portions on the installation for the lower jaw are bent to extend upwardly and said collar portion on the installation in the upper jaw are bent to extend downwardly, in both cases away from the gingiva.

Once the adjustment is obtained which is satisfactory for support without causing discomfort for the patient, the ligature 58 is threaded through the openings 32 or 34 to fix the jaws together as illustrated in FIG. 3. The ligature is fixed with a knot 60. Cross-wiring as shown in FIG. 3 is preferred because this aids in the elimination of front to rear displacement of the teeth in one jaw with respect to the teeth of the other jaw so that any tendency for the patient to be able to jut the lower jaw forward or backward is controlled. Thanks to the right angle orientation between the transverse bore 32 and the transverse bore 34 in each of the retainer members 14 there is always an opening for the ligature conveniently available regardless of the rotational position of the retainer members 14, and this speeds up the installation and makes a neater job.

It is preferable that the anchor member 12 be made of metal, such as stainless steel, in order to have satisfactory strength in small size to fit in the minimum spaces in which the surgeon must work. Preferably any metal used should be similar so as to avoid Galvanic corrosion. It is preferable to make the retainer members out of strong plastic materials although they can also be made of metal.

Figure 5:
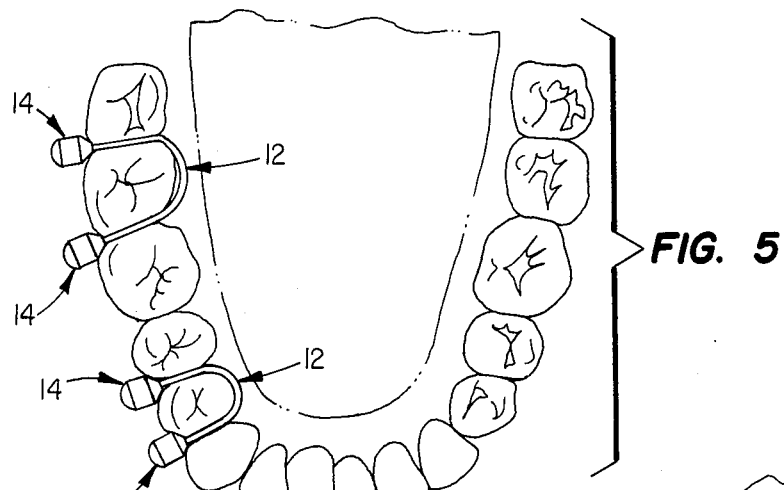
FIG. 5 is a plan view of a jaw showing two of the devices in place on teeth of different size.

FIG. 5 illustrates the installation of two of the devices on the same jaw which illustrates the difference in the size of teeth in the bicuspid area as opposed to the molar area of the jaw for example. It illustrates the fact that more than one set of the devices can be used if necessary. Ordinarily one set of the devices as illustrated in FIG. 3 will suffice to fix the jaw. The anchor members 12 are easily modified to fit different sized teeth.

In the installation of FIG. 6 and 7 the band 46 is preferably made of metal or very strong elastomeric material which is deformable to fit the shape of the teeth. Plastic has the advantage of tending to minimize thermal shock or galvanic currents especially from contact with filling materials in the tooth to which it is attached, so that plastic is preferred. In addition to strength the material must have good tear resistance and the openings 48 and 50 should be neatly rounded to avoid stress points.

It is evident that the assemblies 10, 62 are very simple in design and relatively inexpensive to manufacture but more importantly they simplify the installation so that it requires less time for the surgeon, reduces the patient's time under anesthesia and significantly improves the comfort for the patient in the relatively long period during which the devices are often worn. It is important to note that the device must be firmly anchored to the one selected tooth on each of the opposing jaws to which the anchor members and retainer members are fixed. There should be absolutely no movement of the jaws with respect to each other once the two devices are wired together as indicated in the manner shown in FIG. 3. Looseness or rocking of the leveraged anchor members by reason of forces exerted by the ligature wires 58, 92 on the retainer members 14, 64 is to be avoided so that once the jaws are fixed in position they will remain in exactly the same position during the healing process. It is preferable that the retainer member-anchor member holding means be substantially infinitely variable in adjustment so that a tight grip on an individual tooth will be obtained. A step or incremental type adjustment is undesirable because some looseness is likely to remain after tightening.

The curvature of the collar portion away from the gingiva as illustrated in FIGS. 2 and 10 is extremely important in this regard because of the variation in the shape of teeth which can require positioning the assembly, such as assembly 10 of FIG. 2, in some position other than the horizontal position shown. For example a tooth that was concave and or sloping on the surface in contact with the retainer member 14 might require positioning at an off horizontal angle. Thus the retainer members might be moved upwardly such that the collar member would be moved downward toward the gum line and possibly even in contact with the gingiva if the collar member were not bent upwardly away from the gum area. A similar situation would exist with respect to the assembly 10 on a selected tooth of the upper jaw which would essentially be a mirror image of FIG. 2. The upward curvature of the collar away from the axes through the straight portions 18 of the anchor member 12 greatly reduces the possibility that the collar portion 16 will come in contact with the gingiva when providing a tight lock of device 10 on a selected tooth, such as tooth 22 in FIG. 2.

Infinite adjustment of the retainer member 14 on the legs of the anchor member 12 is most easily accomplished by the means of screw threads on both parts or by having a self threading retainer member material which would still provide sufficient strength to maintain a tight grip on the tooth when the device is tightened in place. A complete fixation of the jaw can be obtained by having a pair of the devices 10 on each of the upper and lower jaws on opposite sides of the jaws and arranged vertically in the manner of FIG. 3. A good tight installation as shown in FIG. 3, on each side of the set jaws can fix the jaws with an absolute minimum of materials and enable the person making the installation to do so neatly and quickly. Due to the small number of parts in the system there is also less chance for any food materials to collect during the period of recovery since the patient cannot brush his teeth but still must eat.

Although preferred embodiments of the present invention have been described herein in detail those skilled in the art will recognize that various substitutions and modifications may be made to the specific structural features of the fixation system shown and described without departing from the scope and spirit of the invention recited in the appended claims.

What I claim is:

1. A jaw fixation assembly for use in oral and maxillofacial surgery and the like for fixation of the jaw structure, comprising:
    a generally "U" shaped anchor member for a selected tooth of each jaw, having two extended spaced apart straight portions joined through a curved collar portion at one end, said straight portions extending opposite said collar portion, said collar portion having a curvature suitable to pass around the lingual side of one selected tooth with said extended straight portions lying along side said one tooth and being interproximally between adjacent teeth, the straight portions of said anchor member having means for retaining a retainer member; and
    retainer members removably attached to each straight portion of said anchor member, having a body portion with an axial bore therethrough including means for adjustably and removably engaging said straight portion of said anchor member, and at least one opening through said retainer member on an axis transverse and offset from said axial bore, said retainer members being tightenable on said anchor member to fasten it securely upon said tooth.

2. The fixation assembly set forth in claim 1 wherein:
    the curved portion of said anchor member joining said straight portions is also curved in another direction away from a plane formed by axes through the legs of the anchor member.

3. The fixation assembly set forth in claim 1 wherein:
    the retainer member body portion is further defined as having an outer head portion and an inner rounded portion, said rounded portion being closest to said curved portion when said assembly is completed.

4. The fixation assembly set forth in claim 1 wherein:
    the curved portion of said anchor member joining said straight portions is also curved in another direction away from a plane formed by axes through the legs of the anchor member; and
    the retainer member body portion is further defined as having an outer head portion and an inner rounded portion, said rounded portion being closest to said curved portion when said assembly is completed.

5. The assembly of claim 4 wherein the means for engaging retainer members constitutes screw threads on said leg portions of said anchor members.

6. A jaw fixation assembly for use in oral and maxillofacial surgery and the like for fixation of the jaw structure, comprising:
    an anchor member for each jaw having a collar portion and opposed spaced apart leg portions, said collar portion being bent away from the axis of said leg portions and being curved to fit around one selected tooth, the spacing of said straight portions being such that with said curved portion in contact with the lingual side of said one tooth said leg portions will lie on opposed sides of said tooth, said leg portions having excess length sufficient to pass through and beyond the interproximal spaces between said one tooth and adjacent teeth and having means for engagement with a bore of a retainer member; and
    retainer members adjustably and removably fastened on each leg portion of said anchor member to tighten said anchor member upon said tooth, said retainer members having a body with an outer end and a rounded inner end and having an axial bore therethrough, said bore having means for adjustably engaging and disengaging the leg portion of said anchor member, said body having at least one ligature bore transverse to said axial bore but offset therefrom.

7. The fixation assembly set forth in claim 6 further comprising:
    compressible "O" rings mountable on the leg portion of an anchor member and adapted to be compressible by retainer members against a portion of a patients tooth to cushion the assembly when said retainer members are tightly installed on said anchor member.

8. The fixation assembly set forth in claim 6 which further includes a deformable band having at least a pair of openings, one through which each leg portion of an anchor member in assembly extends, said band being tensioned against at least a portion of a tooth by said retainer members.

9. The assembly of claim 6 wherein the means for engaging retainer members constitutes screw threads on said leg portions of said anchor members.

10. A jaw fixation assembly for use in oral and maxilofacial surgery and the like for fixation of the jaw structure, comprising:
a "U" shaped wire anchor member adapted to be placed around a selected tooth on each jaw, said member having two spaced apart leg portions connected through a curved collar portion, said collar portion being bent away from axes through the leg portions of the anchor member, said leg portions having means for engaging retainer members; and
retainer members removably attached to each leg portion, said retainer members each having a body with an axial bore therethrough wherein said bore includes means for removably engaging the leg portion of an anchor member, said retainer members being tightenable against the buccal side of the teeth when the anchor members are in place around said one selected tooth, said retainer member body having at least one transverse bore offset from said axial bore, said transverse bore being provided to bind the jaws together by passing ligature wire through the transverse bore of retainer members mounted on anchor members fixed to a said selected tooth in an upper and a lower jaw.

11. The assembly of claim 10 further including a compressible "O" ring for each leg portion of said anchor member, said "O" rings being adapted for passing over the leg portion and its means for engaging the retainer members but small enough to be compressed by a retainer member when tightened against a tooth, and capable of providing a cushioning effect when an anchor member and respective retainer members are installed on a selected tooth, said ring being in partial contact with immediately adjacent teeth.

12. The assembly of claim 10 further including a deformable band having at least two spaced apart openings therein through which in assembly, each of a leg portion may be passed for subsequent installation of said retainer members, said band being deformably tensioned against a portion of a tooth selected for installation of the fixation device when said retainer members are tightened.

13. The assembly of claim 10 wherein the means for engaging retainer members constitutes screw threads on said leg portions of said anchor members.

14. The assembly of claim 11 wherein the means for engaging retainer members constitutes screw threads on said leg portions of said anchor members.

15. A jaw fixation assembly for use in oral and maxilofacial surgery and the like for fixation of the jaw structure, comprising:
a generally "U" shaped anchor member for a selected tooth of each jaw, having two extended spaced apart straight portions joined through a curved collar portion at one end, said straight portions extending opposite said collar portion, said collar portion having a curvature suitable to pass around the lingual side of one selected tooth with said extended straight portions lying along side said one tooth and being interproximally between adjacent teeth, the straight portions of said anchor member having means for retaining a retainer member; and
a retainer member removably attached to each straight portion of said anchor member, having a body portion with an exial bore therethrough adapted for adjustably engaging said straight portion of said anchor member, said retainer member being tightenable on each leg of said anchor member to fasten it securely upon said tooth.

16. The fixation assembly set forth in claim 15 wherein:
the curved collar portion of said anchor member joining said straight portions is also curved in another direction away from a plane formed by axes through the legs of the anchor member.

17. The fixation assembly set forth in claim 15 wherein:
the retainer member body portion is further defined as having an inside rounded portion, said inside rounded portion being closest to said curved portion when said assembly is completed.

18. The fixation assembly set forth in Claim 15 wherein:
the curved collar portion of said anchor member joining said straight portions is also curved in another direction away from a plane formed by axes through the legs of the anchor member; and
the retainer member body portion is further defined as having an inside rounded portion, said inside rounded portion being closest to said curved collar portion when said assembly is completed.

19. The assembly of claim 18 wherein the means for engaging retainer members includes screw threads on said leg portions of said anchor members.

20. The assembly of claim 19 wherein the retainer members include means for connecting ligature wire between retainer members.

21. The assembly of claim 20 wherein the body portion of the retainer members have at least one flat surface parallel to the axis of the bore of said retainer members.

22. The assembly of claim 21 wherein the retainer members further include a pair of opposed flat surfaces on the body between the rounded ends and means for connecting ligature wire on each retainer member which comprises a peripheral groove on the body between the rounded ends.

23. The assembly of claim 22 further including a tool having a handle and a head with means to engage at least one flat surface on a retainer member for rotating said retainer member into engagement with a leg portion of an anchor member.

24. A jaw fixation assembly for use in oral and maxilofacial surgery and the like for fixation of the jaw structure, comprising:
an anchor member for each jaw having a collar portion and opposed spaced apart leg portions, said collar portion being bent away from the axis of said leg portions and being curved to fit around one selected tooth, the spacing of said leg portions being such that with said curved portion in contact with the lingual side of said one tooth said leg portions will lie on opposed sides of said tooth, said leg portions having excess length sufficient to pass through and beyond the interproximal spaces between said one tooth and adjacent teeth and having means for engagement with a bore of a retainer member; and retainer members adjustably fastened on each leg portion of said anchor members to tighten said anchor member upon said tooth, said retainer members having means for binding a retainer member on one jaw to a retainer member on the opposite jaw.

25. The fixation assembly set forth in claim 24 wherein:

the curved collar portion of said anchor member joining said straight portions is also curved in another direction away from a plane formed by axes through the legs of said anchor member.

26. The fixation assembly set forth in claim 25 wherein the retainer member body portion is further defined as having an inside rounded portion, said inside rounded portion being closest to said curved collar portion when said retainer member is engaged on a leg portion of an anchor member.

27. The asesmbly of claim 26 wherein the retainer members include means for connecting ligature wire between retainer members.

28. The assembly of claim 27 wherein the body portion of the retainer members have at least one flat surface parallel to the axis of the bore of said retainer members.

29. The assembly of claim 28 wherein the retainer members further include a pair of opposed flat surfaces on the body between the rounded ends and means for connecting ligature wire on each retainer member which comprises a peripheral groove on the body between the rounded ends.

30. The assembly of claim 29 further including a tool having a handle and a head with means to engage at least one flat surface on a retainer member for rotating said retainer member into engagement with a leg portion of an anchor member.

* * * * *